United States Patent [19]
Plunkett

[11] Patent Number: 5,879,317
[45] Date of Patent: Mar. 9, 1999

[54] ELECTROSTATIC BLOOD DEFOAMER FOR HEART-LUNG MACHINES

[75] Inventor: Sean D. Plunkett, Mission Viejo, Calif.

[73] Assignee: Medtronic, Inc., Minneapolis, Minn.

[21] Appl. No.: 865,218

[22] Filed: May 29, 1997

Related U.S. Application Data

[62] Division of Ser. No. 643,144, Apr. 30, 1996.

[51] Int. Cl.⁶ .................................................. A61M 37/00
[52] U.S. Cl. .................................................. 604/4; 422/44
[58] Field of Search ........................... 604/4–6; 210/748, 210/243, 764; 422/22, 44; 204/131, 186, 164

[56] References Cited

U.S. PATENT DOCUMENTS

| | | | |
|---|---|---|---|
| 4,253,456 | 3/1981 | Schindler et al. .................... 128/214 |
| 4,309,592 | 1/1982 | Le Boeuf ............................... 219/299 |
| 5,139,684 | 8/1992 | Kaali et al. ........................... 210/748 |
| 5,304,164 | 4/1994 | Lindsay ................................. 604/403 |
| 5,545,130 | 8/1996 | Hofmann et al. ....................... 604/4 |
| 5,685,698 | 11/1997 | Smoll ..................................... 417/50 |

OTHER PUBLICATIONS

Sonntag and Strenge, *Coagulation and Stability of Disperse Systems,* Halsted–Wiley, New York, 1972, p. 114.

*Primary Examiner*—Mark O. Polutta
*Assistant Examiner*—Ki Yong O
*Attorney, Agent, or Firm*—Harry G. Weissenberger

[57] ABSTRACT

In a heart-lung machine, blood is defoamed without the use of defoaming chemicals by passing blood between parallel insulated electrodes whose electric field orients the blood protein molecules to break up the foam bubbles. The blood then passes into the venous reservoir through a bubble screen which traps any remaining bubbles.

4 Claims, 2 Drawing Sheets

ELECTROSTATIC BLOOD DEFOAMER FOR HEART-LUNG MACHINES

RELATED CASES

This case is a division of application Ser. No. 08/643,144 filed on Apr. 30, 1996 and entitled "Electrostatic Blood Defoamer for Heart Lung Machines".

FIELD OF THE INVENTION

This invention relates to heart-lung machines, and more particularly to an electrostatic defoamer for defoaming blood in a reservoir.

BACKGROUND OF THE INVENTION

During coronary bypass surgery, the main flow of the patient's blood is conventionally taken from the patient's vena cava, oxygenated in a heart-lung machine, and returned to the patient's aorta. Some blood, however, escapes into the surgical field, where it is conventionally aspirated by a sucker device and returned to the blood bypass circuit of the heart-lung machine through an appropriate filter which removes air bubbles and surgical debris.

A problem with cardiotomy filters is that when blood is aspirated from the surgical field, it is mixed with a great deal of air, which results in the formation of air bubbles. Due to the structure of blood proteins, these bubbles are highly stable. This is so because blood proteins are randomly oriented polar macro-molecules whose random orientation has a strong stabilizing effect. This process is different from the action of chemical stabilizers which are surface active, and it leads to the production of a foam which is difficult to break up by means of the chemical defoamers such as silicone compounds conventionally used in cardiotomy filters.

Quite aside from the difficulty of chemically defoaming cardiotomy blood, the use of defoaming agents in multi-layer filters, which are currently the norm, is physiologically undesirable and is traumatizing to the blood. Also, some foaming occurs as well in the venous reservoir which receives blood from the vena cava, and it would be advantageous not to have to make that blood pass through a defoaming filter. Consequently, there exists a need for a defoamer which is non-invasive, non-traumatizing, inexpensive and disposable, and which has a simple, essentially unobstructed blood path.

SUMMARY OF THE INVENTION

In accordance with the invention, blood is defoamed in a heart-lung machine by passing it through a reservoir in which insulated, electrically charged plates are disposed within a porous restraint through which the blood must flow to enter the main body of the reservoir. The blood circulating within the porous restraint (through which bubbles cannot pass) circulates through the static electric field between the plates, which orders and orients the blood protein molecules to break up the bubbles and make them transient. In a preferred embodiment, the electrostatic field is generated by a series of interleaved, narrowly spaced plates of opposite polarity so as to maximize the voltage gradient between the plates.

DESCRIPTION OF THE PREFERRED EMBODIMENT

Figure 1:
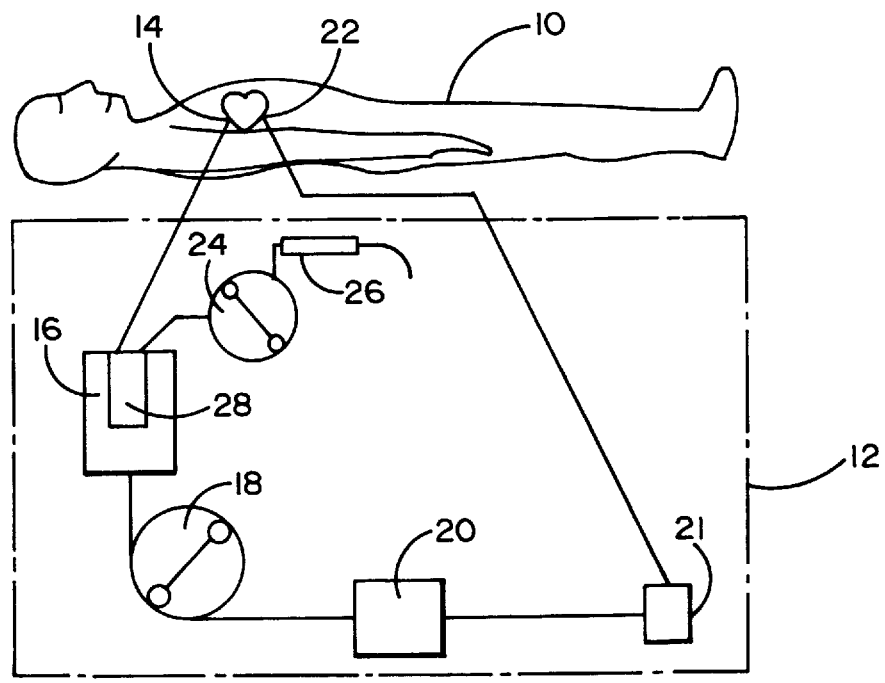
FIG. 1 schematically illustrates a heart-lung machine using the defoamer of this invention.

FIG. 1 shows the environment in which the present invention is useful. During open-heart surgery, the circulatory system of patient 10 is bypassed by a heart-lung machine 12. Essentially, the heart-lung machine 12 diverts the patient's blood from the vena cava 14, passes it through a venous reservoir 16, and uses a pump 18 to pump the blood through an oxygenator 20 and arterial filter back into the patient's aorta 22.

Blood leaking into the surgical field during surgery is pumped from the surgical field by a cardiotomy pump 24 through a suction device 26. The blood thus recovered is filtered in a cardiotomy filter 28 to remove surgical debris, and is then returned to the bypass blood stream in the venous reservoir 16.

In the prior art, the bulk of the voluminous, highly stable foam created by the suction of blood and air from the surgical field was broken up by coating the material of cardiotomy filter 28 with chemical defoaming agents such as silicone compounds. Any remaining air bubbles, as well as any bubbles produced by the blood flow in the venous reservoir 16, were broken up by additional filtration such as at 21 in the bypass blood circuit downstream of the venous reservoir 16.

Filtration of blood through very small-apertured, chemically coated filters is undesirable because it invites hemolysis and thrombus formation, and because it exposes the blood to defoaming agents which, although biocompatible, are nevertheless foreign substances with which contact is best minimized.

Figure 3:
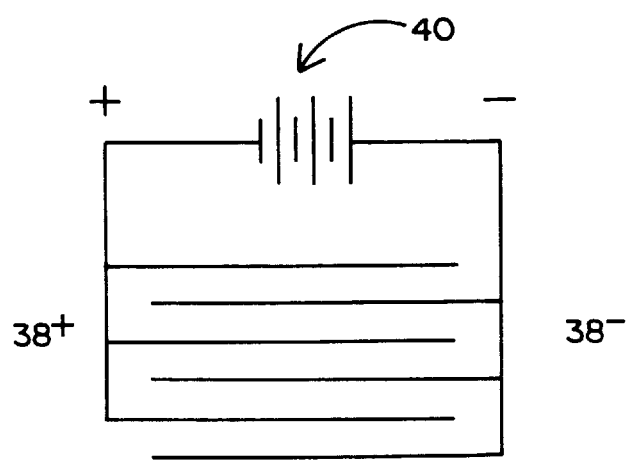
FIG. 3 is a schematic plan view showing the electrical connections of the defoamer plates.
Figure 2:
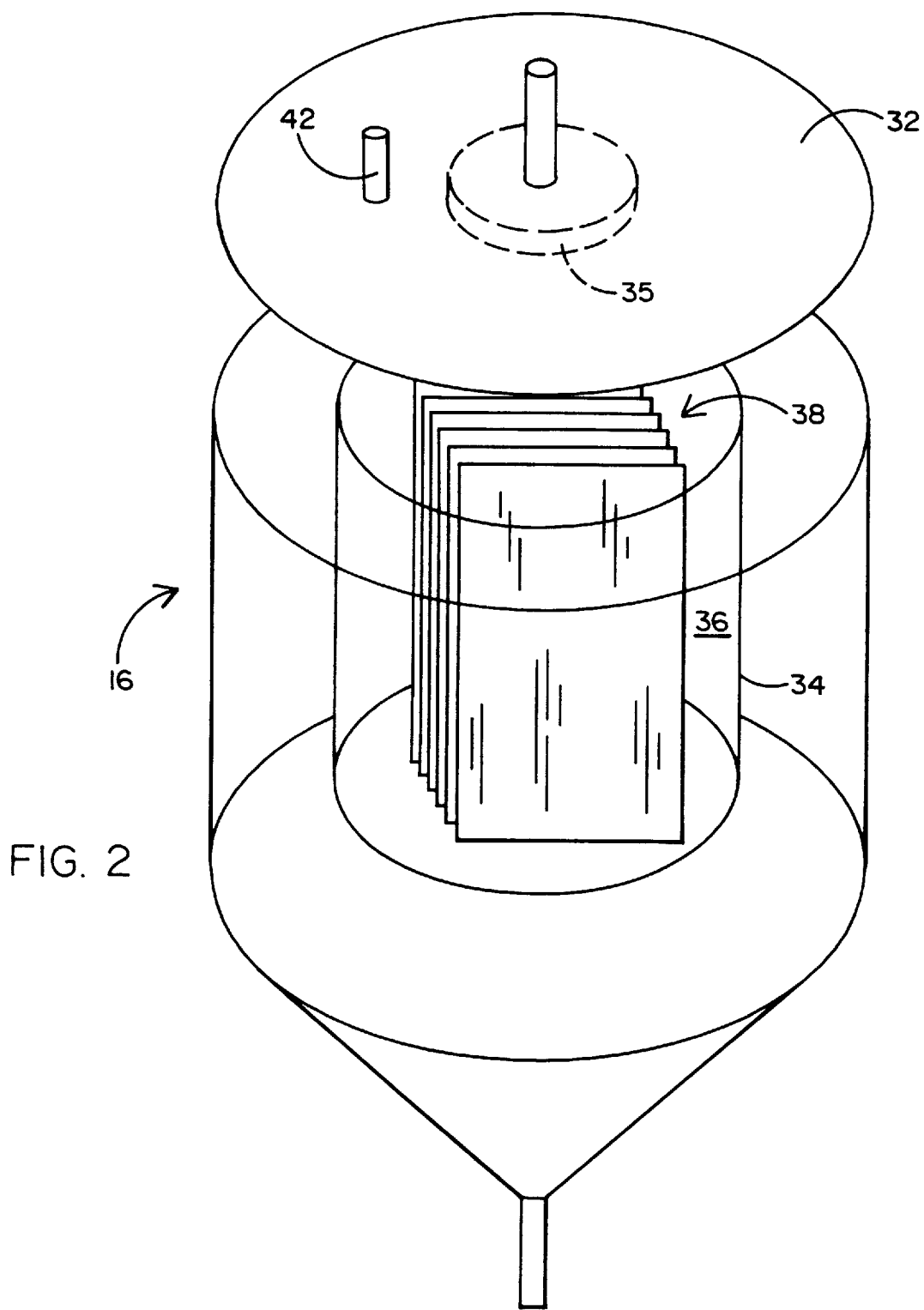
FIG. 2 is a partially exploded schematic view of a defoamer according to the invention.

In a system like that of FIG. 1 using the invention of FIGS. 2 and 3, cardiotomy blood does not need to be defoamed in cardiotomy filter 28 by chemical agents. It is merely necessary to remove surgical debris by a coarse filter which minimizes blood trauma and breaks up very large bubbles. The undefoamed cardiotomy blood and the venous blood from the patient are then brought together and discharged into the inventive reservoir 16 shown in detail in FIG. 2.

The reservoir 16 of FIG. 2 includes a body 30, a cover 32 (shown raised in FIG. 2 as indicated by dotted lines), and a cup-shaped bubble screen 34. With the cover 32 in place to where it contacts the rim of bubble screeen 34, venous and cardiotomy blood are introduced through the inlet manifold 35 into the defoaming chamber 36 formed by the interior of bubble screen 34. Parallel electrodes 38 coated with a smooth-surfaced blood-compatible insulating material such as silicone or polyvinyl chloride are disposed in a generally vertical orientation in the defoaming chamber 36, so that most of the blood entering the reservoir 16 flows down between the electrodes 38.

As best shown in FIG. 3, the electrodes 38 consist of alternating interleaved electrodes $38^+$ and $38^-$, respectively. They are connected to a DC supply 40 represented in FIG. 3 by a battery symbol.

In order to obtain a sufficient electrical field without unduly narrowing the blood path between the electrodes 38, the DC potential applied to the electrodes 38 is preferably several thousand volts at plate spacings of a few millimeters, resulting in a voltage gradient or field strength on the order of $10^4$ V/cm. Field strengths of this general order have been proposed by Sonntag and Strenge, *Coagulation and Stability of Disperse Systems*, Halsted-Wiley, New York, 1972, p. 114 for the breaking of colloid foams in industrial applications.

Defoamed blood exits the defoaming chamber 36 through the bubble screen 34. The bubble screen 34 is of a sufficiently fine mesh to prevent the passage of any remaining bubbles. These recirculate in the defoaming chamber 36 and are eventually broken up. The air removed from the blood in the defoaming chamber 36 is vented to atmosphere by vent 42. The foam-free blood passing through the bubble screen 34 collects in the bottom of reservoir 16 and is then ready to be pumped through the oxygenator 20.

It is understood that the exemplary electrostatic blood defoamer for heart-lung machines described herein and shown in the drawings represents only a presently preferred embodiment of the invention. Indeed, various modifications and additions may be made to such embodiment without departing from the spirit and scope of the invention. Thus, other modifications and additions may be obvious to those skilled in the art and may be implemented to adapt the present invention for use in a variety of different applications.

I claim:

1. A method of defoaming blood in a cardiotomy filter/defoamer having a defoaming chamber receiving blood from a top-mounted inlet and passing it through a filtering and defoaming medium, comprising the steps of:

a) providing in said chamber a set of insulated electrode plates connected to a direct current voltage source so as to produce a static electric field therebetween, and b) causing said blood to pass through said electric field between said inlet and said filtering and defoaming medium.

2. The method of claim 1, in which said electric field has a field strength of substantially $10^4$V/cm.

3. The method of claim 2, in which said set of electrode plates consists of a plurality of interleaved closely spaced electrodes of alternating potential.

4. The method of claim 3, in which blood flow through said electric field is maximized by disposing said electrode plates vertically in said chamber.

* * * * *